United States Patent [19]
Nichols et al.

[11] Patent Number: 5,361,766
[45] Date of Patent: Nov. 8, 1994

[54] QUICK RELEASE BONE PROBE AND X-RAY MARKER

[76] Inventors: David Nichols, 675 Watson, Memphis, Tenn. 38111; David Szalay, 2455 Monroe, Memphis, Tenn. 38112

[21] Appl. No.: 18,092

[22] Filed: Feb. 17, 1993

[51] Int. Cl.⁵ ............................................. A61B 6/12
[52] U.S. Cl. ................................. 128/654; 128/754
[58] Field of Search ................. 128/653.4, 654, 749, 128/751, 753–754; 606/86–88, 97, 99, 102, 104; 604/93, 51

[56] References Cited

U.S. PATENT DOCUMENTS

| | | | |
|---|---|---|---|
| 3,704,707 | 12/1972 | Halloran | 606/97 |
| 4,005,527 | 2/1977 | Wilson et al. | 606/102 |
| 4,986,279 | 1/1991 | O'Neill | 128/754 |
| 5,005,585 | 4/1991 | Mazza | 128/754 |
| 5,013,318 | 5/1991 | Spranza | 606/102 |
| 5,178,164 | 1/1993 | Allen | 606/97 X |
| 5,217,024 | 6/1993 | Dorsey et al. | 128/749 X |

OTHER PUBLICATIONS

Acro Med Product Catalog, Jan. 1991, pp. V-1 and V-2.
Spine: Pedicle Fixation of the Lumbar Spine; David Arnold, M.D. and John Lonstein, M.D. "State of the Art Reviews" vol. 6 No. 1, Jan. 92, p. 66.

Primary Examiner—Angela D. Sykes

[57] ABSTRACT

A surgical instrument for use in spinal implant procedures to enter the pedicle of a vertebrae, comprising a probe having a proximal end and a distal end with fastening means on the proximal end and a handle. The handle has gripping means and further includes fastening means for selectively engaging the proximal end of the probe. The distal end of the probe is shaped to pierce the pedicle of a vertebrae. The probe includes marking means for determining the depth the distal end projects into a pedicle and marking means for selectively distinguishing a right probe from a left probe on interoperative x-rays.

8 Claims, 2 Drawing Sheets

QUICK RELEASE BONE PROBE AND X-RAY MARKER

FIELD OF THE INVENTION

The present invention relates to a surgical instrument for use in spinal implant procedures, and more particularly to a surgical instrument that combines a probe used to enter the pedicle of a vertebrae with an x-ray marker.

BACKGROUND OF THE INVENTION

There are a number of surgical procedures such as laminectomies and discectomies which use appliances for fixing adjacent vertebrae relative to each other. Many of these appliances use bone screws or bone bolts for attaching braces or rods to the vertebrae.

Bone screws are typically implanted into surgical openings formed in the pedicle portions of the vertebrae. After the bone is exposed, a probe is used to form a starting hole in the pedicle and is then removed so that an x-ray marker can be inserted to verify the pedicle hole position through fluoroscopy. After the position of the pedicle hole has been verified, another instrument, a tap, is used to enlarge each hole to an appropriate diameter for the pedicle screw or bone bolt that will be used in the procedure.

Presently known probes have handles formed integral with the probe body or shaft. When these instruments are used, a separate operative step is required for insertion of an x-ray marker. Another probe exists which has a handle that disengages, however, this device does not have depth markings nor an x-ray marker for indicating left and right positions. It would be advantageous to have a bone probe having depth markings with an x-ray marker having an indicator for left and right determinations and a removable handle so that instead of removing a probe and inserting a separate x-ray marker, the handle can simply be removed to achieve the same results.

SUMMARY OF THE INVENTION

The invention is directed to a novel surgical instrument for use in spinal implant procedures that combines a probe used to enter the pedicle of a vertebrae with an x-ray marker without removing the probe from the pedicle hole. The probe has a handle that disengages from the probe shaft with a quick release spring mechanism. The handle has an ergonomically designed spherical gripping portion which fits comfortably in the palm of the surgeon's hand.

The distal end of the probe shaft is flattened into a blade-like tip with a blunt point for piercing a hole in a pedicle. Incremental markings on the probe shaft allow depth control of the probe during insertion into a pedicle. An alternate probe shaft has a metallic marker for indicating the left or right side of a pedicle on interoperative x-rays so the surgeon can easily determine which pedicle side (left or right) he or she is viewing.

The invention is formed of metal materials typically used in surgical instruments which can be sterilized.

BRIEF DESCRIPTION OF THE DRAWINGS

In order to acquire a better understanding of the invention, reference may be had to the detailed description of the exemplary embodiments, set forth below, considered in conjunction with the appended drawings, in which.

DETAILED DESCRIPTION OF PREFERRED EMBODIMENT

Figure 1:
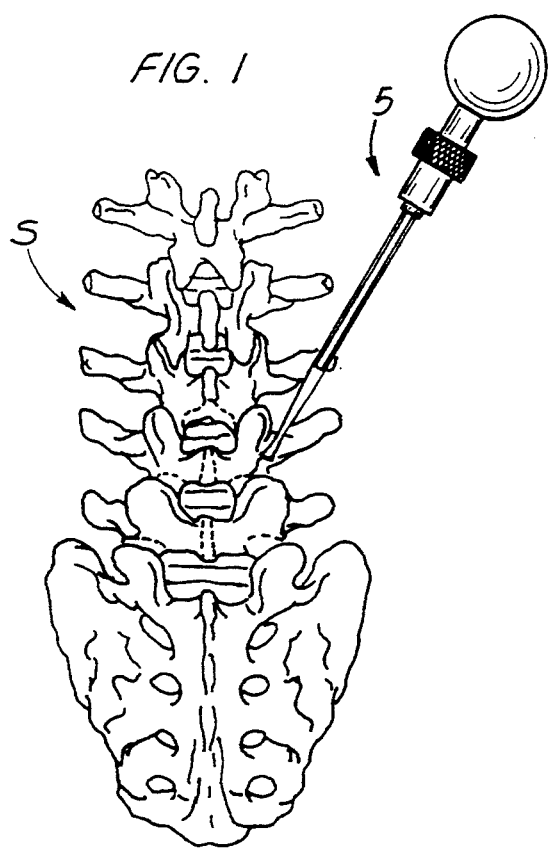
FIG. 1 is a schematic view illustrating the preferred embodiment of the present invention in use a part of a spinal fixation procedure.
Figure 2:
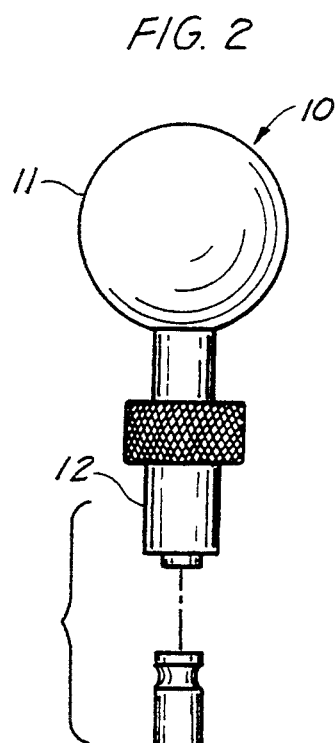
FIG. 2 is a perspective exploded view of the surgical instrument of the present invention.
Figure 3:
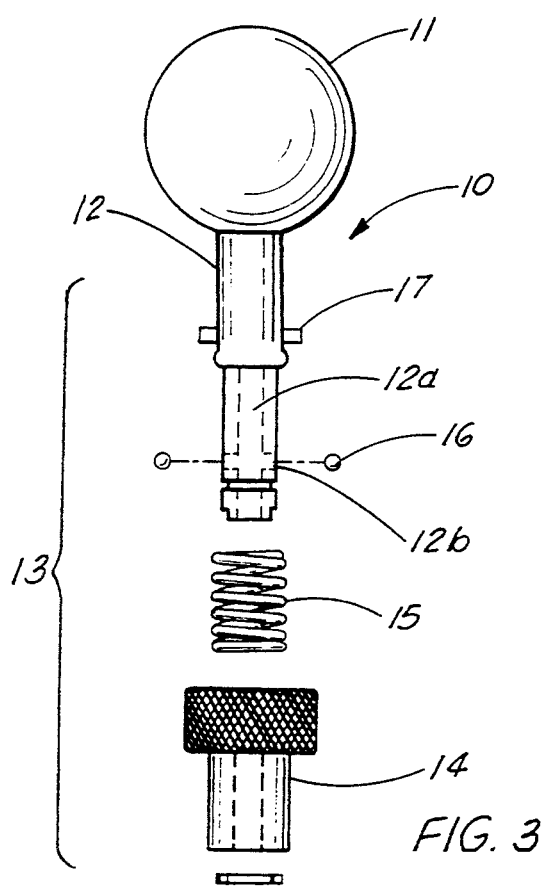
FIG. 3 is a perspective exploded view of the handle of the present invention.

The subject surgical instrument is an improvement on the pedicle probes now in use as it combines both a bone probe having depth markings and an x-ray marker having an indicator for left and right determinations in one instrument with a quick-release handle. As shown in FIG. 2, a surgical instrument 5 is formed with a handle 10 and a shaft 20. The surgical instrument 5 is used to pierce the pedicle of a vertebrae, as shown in FIG. 1, during spinal implant procedures.

Figure 4:
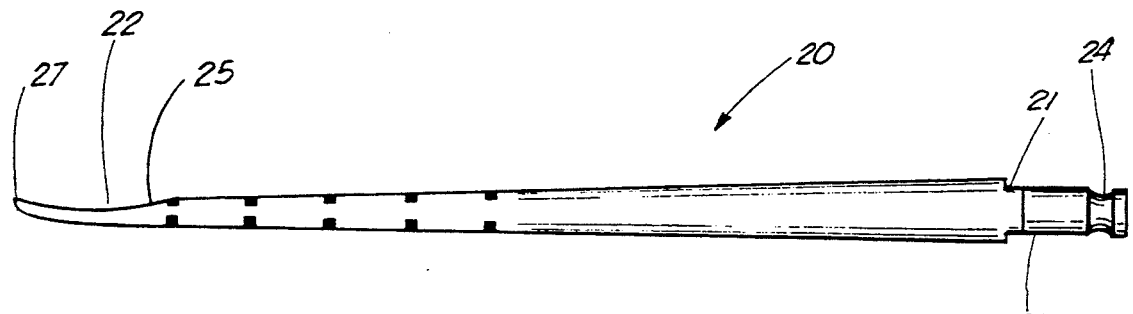
FIG. 4 is a side plan view of the surgical instrument of the present invention.
Figure 5:
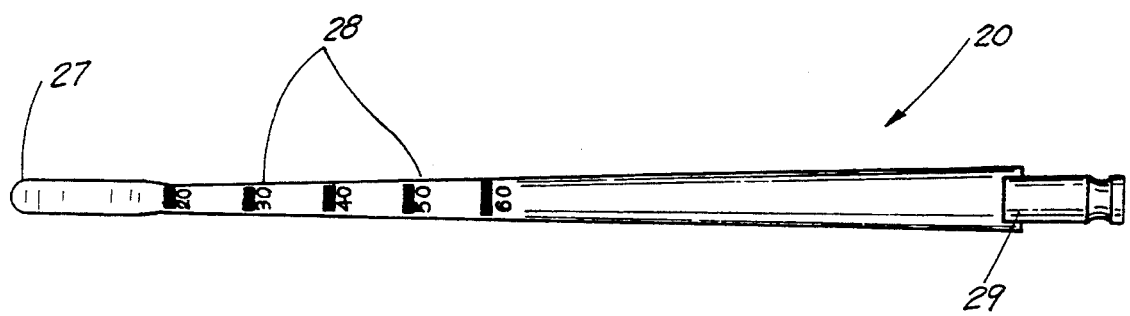
FIG. 5 is a top plan view of the surgical instrument of FIG. 4.

As best illustrated in FIGS. 4 and 5, The shaft 20 has a proximal end 21 and a distal end 22. The shaft 20 is cylindrical in shape and tapers from the proximal end 21 to the distal end 22, the taper ending at point 25 which forms a transition from the shaft 20 to a blade-like portion 26.

The proximal end 21 has an engagement section 23 which is of a smaller diameter than the adjacent shaft 20. An annular grove 24 formed on the engagement section 23 engages the quick release mechanism of the handle 10 described in greater detail below. A ledge 29 is formed on the engagement section 23, for engaging with the quick release mechanism of the handle 10. The distal end 22 flattens into a blade-like portion 26 with a blunt tip 27 for piercing a pedicle. The shaft 20 has markings 28 along two sides of the lower portion of the shaft 20 for determining the depth the shaft 20 is inserted into a pedicle.

The markings 28 are incremental distance markings that measure distance from the tip 27. The markings 28 allow the surgeon to know how far into the pedicle of a vertebrae the shaft 20 is being inserted. The markings 28 on the shaft 20 can best be seen in FIG. 5. In a preferred embodiment the shaft 20 is formed of stainless steel.

The handle 10 has a gripping portion 11 and a tube portion 12 with an opening 12a. The gripping portion 11 is shaped to conform to the palm of a human hand and in a preferred embodiment is spherical. The spherical shape of the gripping portion 11 allows the surgeon a better feel for probe insertion as the blunt tip 27 pierces the pedicle. The tube portion 12 extends longitudinally from the gripping portion 11 and contains a quick release spring mechanism 13. In a preferred embodiment the gripping portion is formed of 6061-T6 aluminum.

The quick release spring mechanism 13 is formed of a slider portion 14, a coil spring 15, two balls 16, and stop bars 17. The coil spring 15 fits inside the slider portion 14, allowing the slider portion 14 to be pulled toward the stop bars 17. The balls 16 are movably mounted in opening 12b. Movement of the slider portion 14 allows the balls 16 to move into and out of the opening 12b. To insert or release the shaft 20 from the handle 10, the slider portion 14 is pulled toward the stop bars 17, allowing the balls 16 to move out of the opening 12b.

When the fastening portion 23 of the shaft 20 is inserted into opening 12a of the tube 12, the slider portion 14 is released forcing the balls 16 back into the opening 12b. The balls 16 fit tightly against the recessed band 24 of the fastening portion 23 on the shaft 20, securing the shaft 20 in the handle 10.

Figure 6:
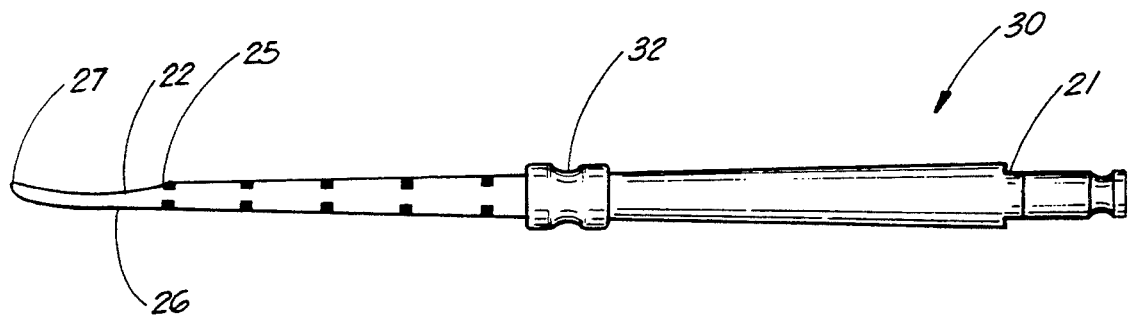
FIG. 6 is a side plan view of an alternate embodiment of the surgical instrument of the present invention.
Figure 7:
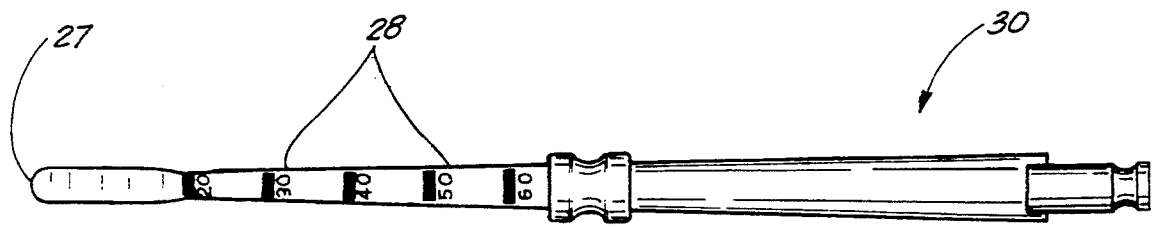
FIG. 7 is a top plan view of the surgical instrument of FIG. 6.

A alternate embodiment of the present invention is shown in FIGS. 6 and 7. A shaft 30 includes the same features as the shaft 20 and further includes a metallic marker 32. The metallic marker 32 is formed to encircle the shaft 30 at about the mid-point between the proximal end 21 and the distal end 22. When the surgical instrument 5 is used as an x-ray marker, the metallic marker 32 functions as an indicator that allows the surgeon to distinguish between the left and right side of a pedicle on interoperative x-rays. For example, the surgeon would use an instrument 5 with shaft 20 on the right side of a pedicle and an instrument 5 with shaft 30 on the left side of a pedicle. The metallic marker 32 on shaft 30 would indicate the left side of the pedicle on interoperative x-rays.

In spinal screw insertion procedures interoperative x-rays are used to verify the position of the pedicle hole. Typically the bone probes are removed and replaced with x-ray markers because the bone probe handles interfere with the x-rays. Additionally, the gripping portion of a bone probe is relatively heavy which tends to cause instability of the bone probe when it projects from a pedicle and is not held by the surgeon. With the subject invention, the handle 10 can easily and quickly be disengaged from the shaft 20 or 30 allowing the shaft 20 and 30 to be used as an x-ray marker rather than having to remove the bone probe 5 and replace it with a separate x-ray marker. Because the handle 10 can be quickly released from the shaft 20 and 30, the surgical instrument 5 can be used as both a probe having depth markers and an x-ray marker having an indicator for left and right side determination.

The quick release handle and probe of the present invention eliminates the operative steps of having to remove the probe and replace it with a marker, by simply allowing the surgeon to remove the quick release handle to achieve the same results. This streamlines the operation by saving time and eliminating a step in the screw insertion procedure.

It should be understood that the foregoing description is exemplary of the invention and not restricted and that improvements and modifications can be made to the invention without departing from the spirit and scope of the invention as defined in the appended claims.

What is claimed is:

1. A surgical instrument for use in spinal implant procedures to enter the pedicle of a vertebrae, comprising:
   a) a probe having a proximal end and a distal end, the probe being generally round in cross-section and tapering from a larger diameter at the proximal end to a smaller diameter at the distal end;
   b) the probe including a fastening means on the proximal end;
   c) a handle having a gripping means and further including fastening means for selectively engaging the proximal end of the probe, said fastening means including spring means which allows for quick release of the probe;
   d) the distal end of the probe being shaped to pierce the pedicle of a vertebrae; and
   e) the probe further including marking means for determining the depth the distal end projects into a pedicle.

2. The surgical instrument of claim 1, wherein the fastening means on the probe comprises a recessed portion shaped for releasably engaging the fastening means of the handle.

3. The surgical instrument of claim 1, wherein the handle gripping means comprises a sphere shaped to conform to the palm of a human hand.

4. The surgical instrument of claim 1, wherein the distal end comprises a tip having a blade-like shape with a blunt point for piercing a pedicle.

5. The surgical instrument of claim 1, wherein the marking means comprises incremental marking on the probe to allow depth control during probe insertion into a pedicle.

6. The surgical instrument of claim 1, wherein, a second marking means is provided for selectively distinguishing a right probe from a left probe on interoperative X-rays, the marking means being formed from a metallic material.

7. A surgical instrument for use in spinal implant procedures to enter the pedicle of a vertebrae, comprising:
   a) a probe having a proximal end and a distal end, the probe being generally round in cross-section and tapering from a larger diameter at the proximal end to a smaller diameter at the distal end;
   b) the probe including a fastening means on the proximal end;
   c) a handle having a gripping means and further including fastening means for selectively engaging the proximal end of the probe, said fastening means including spring means which allows for quick release of the probe;
   d) the distal end of the probe being shaped to pierce the pedicle of a vertebrae; and
   e) the probe further including marking means for selectively distinguishing a right probe from a left probe on interoperative X-rays, the marking means being formed from a metallic material.

8. A surgical instrument for use in spinal implant procedures to enter the pedicle of a vertebrae, comprising:
   a) a probe having a proximal end and a distal end;
   b) the probe including a fastening means on the proximal end;
   c) a handle having a gripping means and further including fastening means for selectively engaging the proximal end of the probe;
   d) the distal end of the probe being shaped to pierce the pedicle of a vertebrae;
   e) the probe further including marking means for determining the depth the distal end projects into a pedicle; and
   f) the probe further including a second marking means for selectively distinguishing a right probe from a left probe on interoperative X-rays, the marking means being formed from a metallic material.

* * * * *